(12) United States Patent
Miesel

(10) Patent No.: US 7,320,676 B2
(45) Date of Patent: Jan. 22, 2008

(54) PRESSURE SENSING IN IMPLANTABLE MEDICAL DEVICES

(75) Inventor: Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 411 days.

(21) Appl. No.: 10/836,115

(22) Filed: Apr. 30, 2004

(65) Prior Publication Data

US 2005/0075624 A1  Apr. 7, 2005

Related U.S. Application Data

(60) Provisional application No. 60/508,020, filed on Oct. 2, 2003.

(51) Int. Cl.
*A61M 31/00* (2006.01)

(52) U.S. Cl. .................. 604/67; 604/505; 604/503; 604/65

(58) Field of Classification Search .. 604/890.1–892.1, 604/503, 505, 65–67, 131
See application file for complete search history.

(56) References Cited

U.S. PATENT DOCUMENTS

| | | | |
|---|---|---|---|
| 3,882,443 A | 5/1975 | Mortia | |
| 4,388,833 A | 6/1983 | Kuwayama | |
| 5,006,997 A | 4/1991 | Reich | |
| 5,279,544 A | 1/1994 | Gross et al. | |
| 5,342,298 A | 8/1994 | Michaels et al. | |
| 5,535,752 A | 7/1996 | Halperin et al. | |
| 5,605,545 A | 2/1997 | Nowosielski et al. | |
| 5,893,838 A | 4/1999 | Daoud et al. | |
| 5,899,873 A | 5/1999 | Jones et al. | |
| 5,928,195 A | 7/1999 | Malamud et al. | |

(Continued)

FOREIGN PATENT DOCUMENTS

EP  1 342 481  9/2003

(Continued)

OTHER PUBLICATIONS

International Search Report, Appl. No. PCT/US04/032579, mailed Jun. 6, 2005 (4 pgs.).

*Primary Examiner*—Kevin C. Sirmons
*Assistant Examiner*—Elizabeth MacNeill
(74) *Attorney, Agent, or Firm*—IPLM Group, P.A.

(57) ABSTRACT

An implantable medical device for delivering a therapeutic substance to a delivery site in a patient. A reservoir holds a supply of the fluid therapeutic substance. A catheter has a proximal end, a delivery region and a lumen extending from the proximal end to the delivery region. The proximal end of the catheter is operatively coupled to the reservoir. The delivery region of the catheter is adapted to be placed proximate the delivery site in the patient. The therapeutic substance is adapted to be delivered through the lumen to the patient. A sensing device is operatively coupled with the lumen of the catheter being capable of detecting a pressure of the therapeutic substance in the lumen. A controller is operatively coupled to the sensing device, the controller being capable of taking an action in response to the pressure in the lumen.

41 Claims, 11 Drawing Sheets

U.S. PATENT DOCUMENTS

| | | |
|---|---|---|
| 6,203,523 B1 | 3/2001 | Haller et al. |
| 6,241,704 B1 * | 6/2001 | Peterson et al. ............... 604/65 |
| 6,394,986 B1 * | 5/2002 | Millar ........................ 604/264 |
| 6,551,290 B1 | 4/2003 | Elsberry et al. |
| 6,740,059 B2 * | 5/2004 | Flaherty ...................... 604/67 |

FOREIGN PATENT DOCUMENTS

| | | |
|---|---|---|
| EP | 0 993 268 B1 | 11/2005 |
| WO | WO 99/55225 | 11/1999 |
| WO | WO 02/070047 A1 | 9/2002 |

* cited by examiner

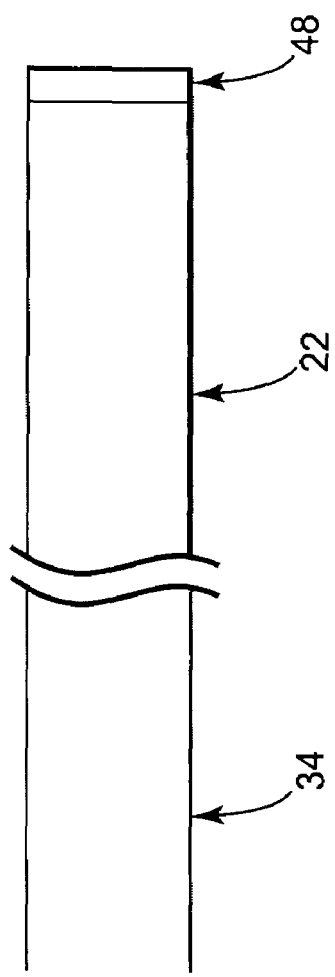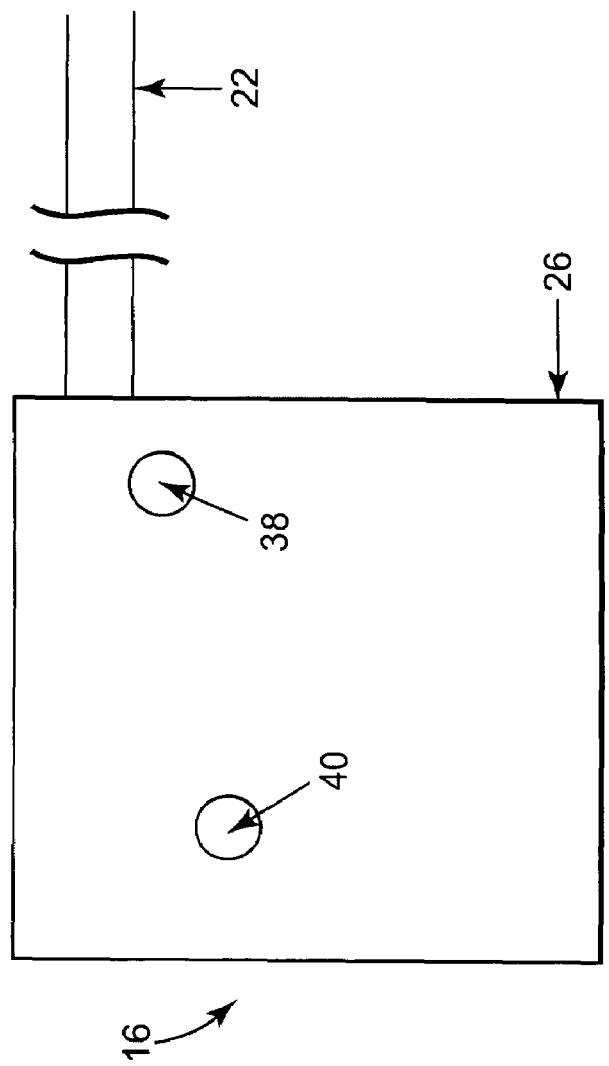

PRESSURE SENSING IN IMPLANTABLE MEDICAL DEVICES

FIELD OF THE INVENTION

The present invention relates generally to pressure sensing in implantable medical devices and, more particularly, to pressure sensing in implantable medical devices delivering a therapeutic substance to a patient.

BACKGROUND OF THE INVENTION

Implantable drug delivery or infusion devices and/or systems are commonly used, for example when chronic administration of a pharmaceutically active agent or therapeutic substance to a patient is required. An implantable infusion pump-catheter delivery system may be preferred when it is important to deliver the agent to a specific site or when the agent must be administered to spaced sites in tightly controlled, yet minute dosages.

Typically, an implantable therapeutic substance delivery device has a reservoir for holding a supply of therapeutic substance awaiting delivery to a delivery site in the patient. A pump may be fluidly coupled to the reservoir for creating fluidic pressure to facilitate delivery of the therapeutic substance to the patient. A catheter provides a pathway for delivering the therapeutic substance to the delivery site in the patient.

All parts of the therapeutic substance delivery device/system need to operate adequately to ensure proper functioning of the device/system. While perhaps the least complex, catheters can have and can develop operational problems.

Sometimes catheters in such delivery systems can become obstructed or clogged. A partial or complete blockage could prevent the therapeutic substance from reaching the delivery site in the patient or, in the case of a partial obstruction, could prevent an adequate supply of the therapeutic substance from reaching the delivery site in the patient.

Catheters can also leak due to cuts, tears, etc. A leak, small or large, can also prevent the therapeutic substance from reaching the delivery site in the patient. A leak can result in a double problem. In addition to the lack of therapeutic substance supplied to the delivery site of the patient, the therapeutic substance could be dispersed elsewhere in the body of the patient which may create further issues.

When catheters become clogged or leak and the infusion pump continues to deliver drug, a patient's well being may be placed in danger.

However, it has been difficult to detect the malfunction of a catheter. For example, if the catheter has a leakage, the implantable drug delivery device could continue to delivery therapeutic substance and there may be no way to know that the therapeutic substance was not reaching the desired delivery site. The patient may not receive the benefit of the therapeutic substance but might not know why. As another example, if the catheter has an obstruction, the implantable drug delivery device might cease to deliver the therapeutic substance. But it may be difficult to know why the failure occurred. The failure to deliver might have been caused by other factors, such as power failure, pump failure or an empty reservoir.

If a catheter malfunctions, it is desirable to know so that appropriate corrective action can be taken.

BRIEF SUMMARY OF THE INVENTION

The present invention can detect a malfunction in a catheter and take appropriate action if and when the malfunction occurs. By the sensing of pressure in the lumen of the catheter, cuts and leaks might result in lower than normal pressure, the lack of appreciable pressure or the lack of a pressure increase. An obstruction might result in higher than normal pressure or a slower than normal pressure decay.

In one embodiment, the present invention provides an implantable medical device for delivering a therapeutic substance to a delivery site in a patient. A reservoir holds a supply of the fluid therapeutic substance. A catheter has a proximal end, a delivery region and a lumen extending from the proximal end to the delivery region. The proximal end of the catheter is operatively coupled to the reservoir. The delivery region of the catheter is adapted to be placed proximate the delivery site in the patient. The therapeutic substance is adapted to be delivered through the lumen to the patient. A sensing device is operatively coupled with the lumen of the catheter being capable of detecting a pressure of the therapeutic substance in the lumen. A controller is operatively coupled to the sensing device, the controller being capable of taking an action in response to the pressure in the lumen.

In another embodiment, the present invention provides a method of delivering a therapeutic substance to a delivery site in a patient. The therapeutic substance is pumped under pressure from a reservoir through a catheter fluidly coupled to the reservoir. The catheter has a proximal end, a delivery region and a lumen extending between the proximal end and the delivery region. The delivery region of the catheter is placed in proximity to the delivery site in the patient. A pressure of the therapeutic substance is detected in the lumen. An action is taken in response to the pressure in the lumen.

In a preferred embodiment, the therapeutic substance is a fluid.

In a preferred embodiment, the therapeutic substance is a liquid.

In another embodiment, the present invention provides a drug delivery system for delivering a liquid therapeutic substance to a delivery site in a patient. An implantable medical device has a reservoir holding a supply of the fluid therapeutic substance and a pump fluidly coupled to the reservoir, the pump being capable of fluidly driving the therapeutic substance to the delivery site under pressure. A catheter has a proximal end, a delivery region and a lumen extending from the proximate end to the delivery region. The proximal end of the catheter is operatively coupled to the pump. The delivery region of the catheter is adapted to be placed proximate the delivery site in the patient. The therapeutic substance is adapted to be delivered through the lumen to the patient. A sensing device is operatively coupled with the lumen of the catheter being capable of detecting a pressure of the therapeutic substance in the lumen. A controller is operatively coupled to the sensing device, the controller being capable of taking an action in response to the pressure in the lumen.

In a preferred embodiment, the sensing device is further capable of detecting a reference pressure outside of the lumen and the controller is capable of taking action in response to relative pressures between the pressure in the lumen and the reference pressure outside of the lumen.

In a preferred embodiment, the location outside of the lumen is in proximity to the implantable medical device.

In a preferred embodiment, the location outside of the lumen is in proximity to the delivery region of the catheter.

In a preferred embodiment, the catheter has a second lumen and the location outside of the first lumen is in the second lumen.

In a preferred embodiment, the location outside of the lumen is outside of the patient.

In a preferred embodiment, action is taken when the pressure exceeds a predetermined level.

In a preferred embodiment, action is based upon an obstruction in the lumen.

In a preferred embodiment, the lumen of the catheter has a restriction and the sensing device is positioned between the reservoir and the restriction.

In a preferred embodiment, action is taken when the pressure drops below a predetermined level.

In a preferred embodiment, action is taken when the pressure has a characteristic signature.

In a preferred embodiment, the characteristic signature follows a transient in delivery rate of the therapeutic substance.

Further, it can be considerably difficult to detect pressure anomalies in catheter malfunctions because the pressure differences are relatively small. For example, the pressure irregularities in a catheter malfunction can be smaller than normal pressure changes due to a change in elevation, e.g., changes in relative elevation as from lying down to standing up. There exists a need for a highly accurate pressure sensor capable of detecting very small pressure differences.

In another embodiment, the present invention provides a sensor for a medical device for detecting pressure in a lumen of a catheter. A base has a first side and a second side. A first pressure sensing diaphragm is operatively coupled to the first side of the base. A second pressure sensing diaphragm is operatively coupled to the second side of the base. A connector having a first end is operatively coupled to a movable portion of the first pressure sensing diaphragm and a second end is operatively coupled to a movable portion the second pressure sensing diaphragm. The connector moves with the first pressure sensing diaphragm and the second pressure sensing diaphragm in response to a change in pressure. An electrical element is responsive to movement of the first pressure sensing diaphragm and the second pressure sensing diaphragm.

In a preferred embodiment, the electrical element is both a first electrical sensor producing a first output in response to movement of the first pressure sensing diaphragm and a second electrical sensor producing a second output in response to movement of the second pressure sensing diaphragm. The first output and the second output are combined to produce a pressure output.

In a preferred embodiment, the first electrical sensor is a first capacitor and wherein the second electrical sensor comprises a second capacitor, wherein a capacitance of the first capacitor is a function of a displacement of the first diaphragm and wherein a capacitance of the second capacitor is a function of a displacement of the second diaphragm.

In a preferred embodiment, a first electrical sensor is a first secondary coil and a second electrical sensor is a second secondary soil. A fluctuating electrical current is induced in a primary coil. The current induced in the first secondary coil and in the second secondary coil by inductive coupling from the primary coil is proportional to a position of the magnetic element which in turn is a function of a displacement of the first diaphragm and the second diaphragm.

BRIEF DESCRIPTION OF THE DRAWINGS

FIG. 3 is a block diagram of a catheter containing a restriction in accordance with a preferred embodiment of the present invention;

FIG. 4 is a drawing illustrating an exterior view of a drug delivery system of an embodiment of the invention;

DETAILED DESCRIPTION OF THE INVENTION

Figure 1:
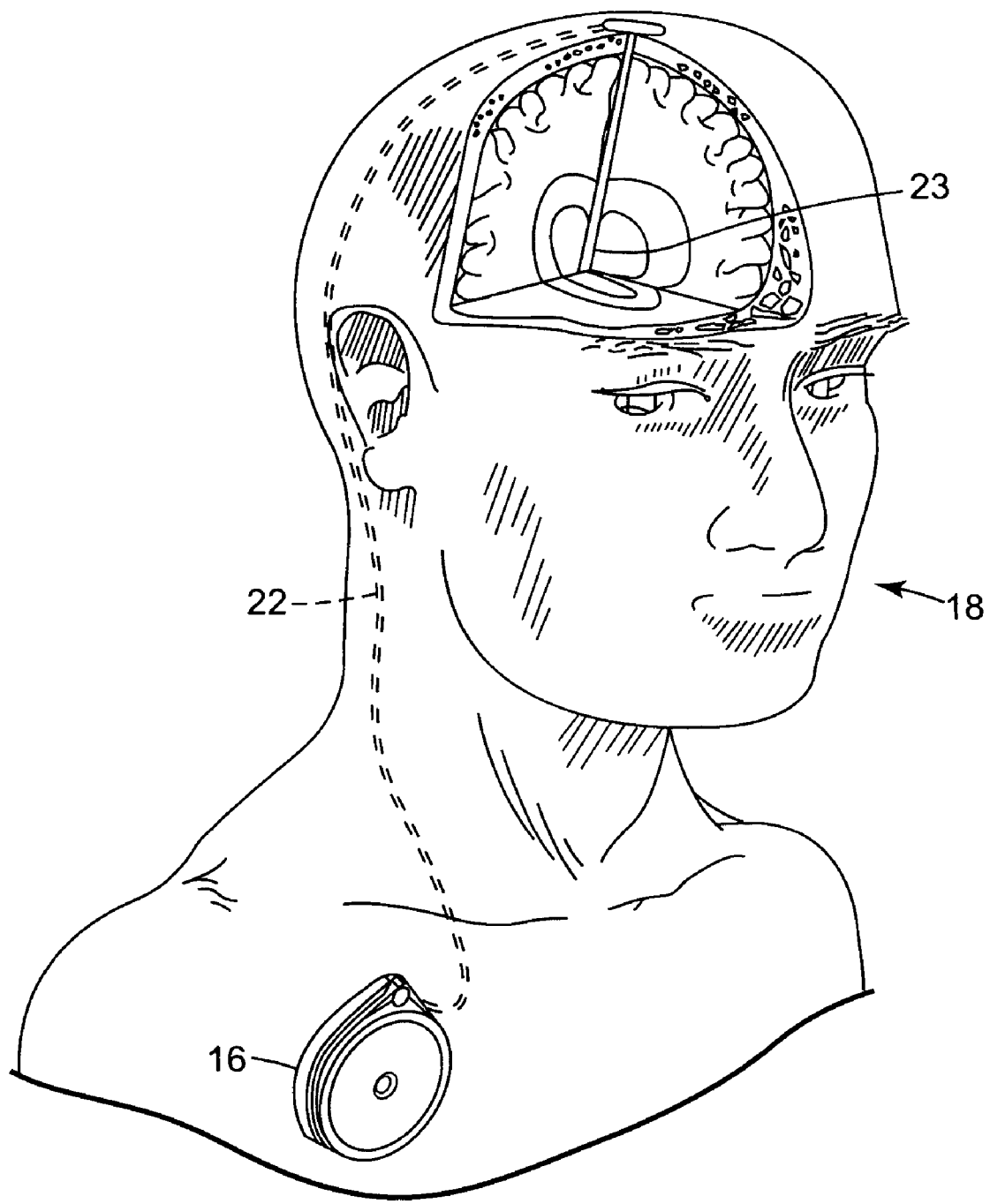
FIG. 1 illustrates an implantable medical device in accordance with an embodiment of the present invention.

FIG. 1 shows implantable medical device 16, for example, a drug pump, implanted in patient 18. The implantable medical device 16 is typically implanted by a surgeon in a sterile surgical procedure performed under local, regional, or general anesthesia. Before implanting the medical device 16, a catheter 22 is typically implanted with the distal end position at a desired therapeutic delivery site 23 and the proximal end tunneled under the skin to the location where the medical device 16 is to be implanted. Catheter 22 may disgorge therapeutic substance at other than at its distal end. For example, catheter 22 may intentionally have a delivery region that is not proximate its distal, e.g., a hole or valve positioned somewhere before reaching the distal end of the catheter 22. Thus, catheter 22 may be placed in patient 18 with a delivery region of catheter 22 placed in or near to, generally proximate to, delivery site 23.

Implantable medical device 16 is generally implanted subcutaneously at depths, depending upon application and device 16, of from 1 centimeter (0.4 inches) to 2.5 centimeters (1 inch) where there is sufficient tissue to support the implanted system. Once medical device 16 is implanted into the patient 18, the incision can be sutured closed and medical device 16 can begin operation.

Implantable medical device 16 operates to infuse a therapeutic substance into patient 18 through catheter 22 to delivery site 23. Implantable medical device 16 can be used for a wide variety of therapies such as pain, spasticity, cancer, and many other medical conditions.

The therapeutic substance contained in implantable medical device 16 is a substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances may or may not be intended to have a therapeutic effect and are not easily classified such as saline solution, fluoroscopy agents, disease diagnostic agents and the like. Unless otherwise noted in the following paragraphs, a drug is synonymous with any therapeutic, diagnostic, or other substance that is delivered by the implantable infusion device.

Figure 2:
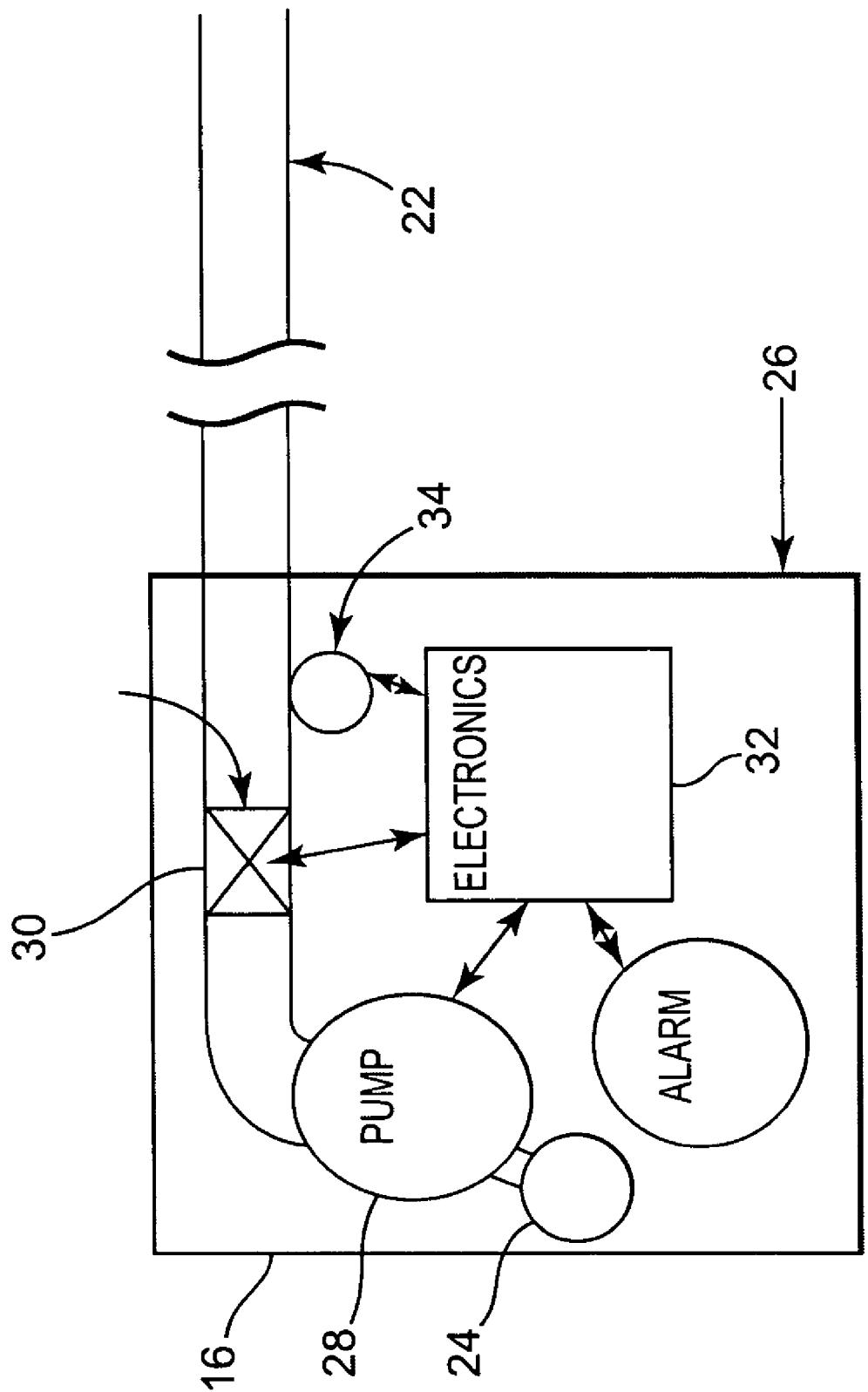
FIG. 2 is a block diagram the implantable medical device of FIG. 1.
Figure 10A:
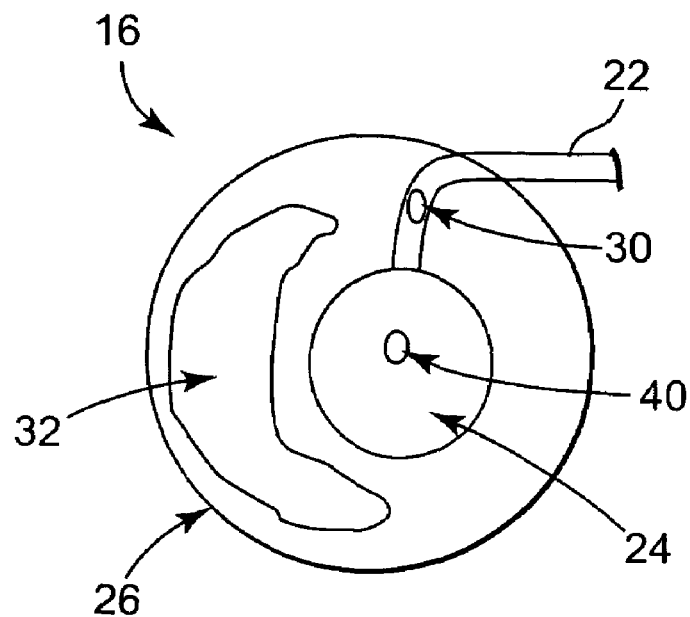
FIG. 10A is a prior art drug delivery system without a pressure sensor.
Figure 10B:
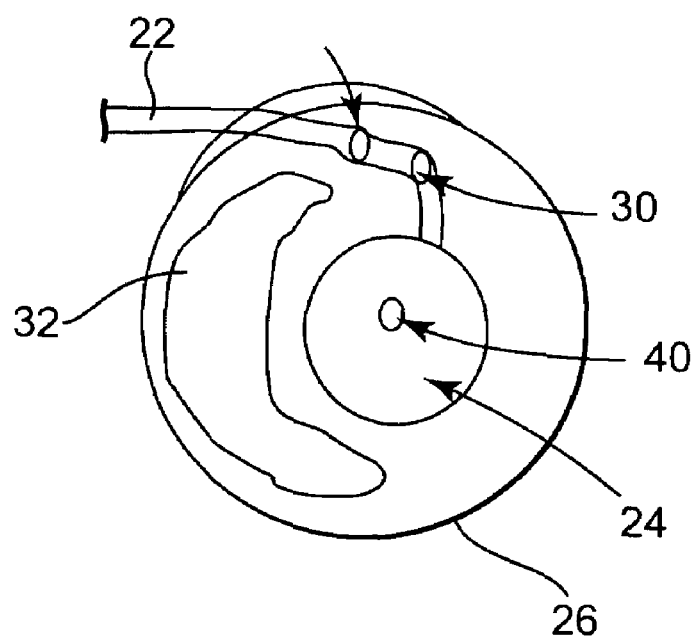
FIG. 10B is a drug delivery system with a pressure sensor in accordance with an embodiment of the invention.

If catheter 22 malfunctions, i.e., has or develops a leak or an obstruction, that malfunction may be detected by analyzing the pressure of the therapeutic substance, typically a fluid and more typically a liquid, in a lumen of catheter 22. FIG. 2 illustrates, in block diagram form, an implantable medical device 16. Implantable medical device is also shown in FIG. 10A and FIG. 10B. Therapeutic substance is stored in reservoir 24 in housing 26. Pump 28 is fluidly coupled to reservoir 24 gaining access to therapeutic substance. The output of pump 28 is coupled to catheter 22 through a check valve 30. Pump 28 and check valve 30 are controllable by electronics module 32. Pressure sensor 34 is operatively coupled to detect/sense pressure in a lumen of catheter 22. If the pressure sensed by pressure sensor 34 is not appropriate, then electronics module 32 may take appropriate action such as by sounding alarm 36. Refill port (see FIG. 4) may be used to refill reservoir 24 without explanting implantable medical device 16.

To detect pressure within catheter 22, pressure sensor 34 may be placed in fluid contact with a lumen of catheter 22. Pressure sensor 34 may be placed in fluid contact with a lumen of a catheter 22 anywhere along the lumen of the catheter 22. In an embodiment, where catheter 22 is coupled to implantable pump 28, pressure sensor 34 may be contained within housing 26. Pressure sensor 34 could also be located external to housing 26. Pressure sensor 34 may be coupled to electronics module 32. For ease of coupling pressure sensor 34 to electronics module 32, it may be preferred to locate pressure sensor 34 within housing 26. Electronics module 32 may also be located in housing 26. Electronics module 32 may control pump 28 and may be coupled to pressure sensor 34. Electronics module 32 may stop pump 28 from continuing to deliver therapeutic substance when a predetermined pressure is detected in catheter 22, which pressure is indicative of a leak in or obstruction of catheter 22.

In certain circumstances it may be desirable to obtain a relative pressure within lumen of catheter 22. That is, it may be preferable to compare a pressure within catheter 22 to a pressure not in catheter 22 to avoid false indications of a leaky or obstructed catheter 22. For example, a pressure reading falsely indicating a leaky catheter may be obtained when catheter 22 is subjected to decreasing atmospheric pressure (e.g., when a subject having an implanted catheter with a pressure sensor goes up an elevator or flies in an airplane). Similarly, a pressure reading falsely indicating that an obstruction exists within catheter 22 may result when catheter 22 is subject to increasing atmospheric pressure (e.g., when a subject having an implanted catheter with a pressure sensor goes scuba diving). To avoid false indications of an obstructed or leaky catheter, it may be desirable to compare a pressure within catheter 22 to a pressure not within catheter 22, preferably within the vicinity of catheter 22. Thus, the pressure not within catheter 22 may be used as a reference pressure.

A reference pressure may be detected within a patient's 18 body in which catheter 22 is implanted or may be detected outside of patient's 18 body. When detected within a patient's body, a reference pressure may be detected in a location near catheter 22 or a location in a separate area of the patient's 18 body. A reference pressure may be obtained in any location capable of providing a pressure indicative of the external environment of implanted catheter 22.

For example, a reference pressure may be taken in or around (in the proximity of) implantable medical device 16, i.e., in a region of a subject's body cavity where a pump system is implanted. This location may be preferred because the reference pressure may be taken without transporting (either before or after measurement) the pressure from a distant location back to implantable medical device 16. For example, FIG. 4 illustrates an implantable pump system having a housing 26 with a vent 38 through which a reference pressure may be obtained.

It is preferred to take a reference in or around (in the proximity of or in the proximate area) delivery site 23. This is the best reference location because therapeutic substance is to be dispensed at this location. Any elevation difference between the delivery site 23 and the reference location would be eliminated by having the reference location at the delivery site 23. Of course, a reference pressure could be taken outside of the patient 18. This may be preferred, for example, when implantable medical device 16 reports the pressure taken in catheter to an external device for adjustment to relative and, perhaps, subsequent appropriate action. This location would eliminate the need for an implanted pressure sensor for a relative pressure measurement and would still account for changes in atmospheric pressure.

Alternatively, a drug delivery system (implantable medical device 16) contains catheter 22 having a lumen for delivering a pharmacological agent (therapeutic substance) and a second lumen through which no pharmacological agent (therapeutic substance) is delivered. A reference pressure may then be detected in the second lumen. The second lumen in catheter 22 can easily be used to obtain a reference pressure from a distal end of catheter 22, from a delivery region of catheter 22 and/or from delivery site 23.

Figure 11:
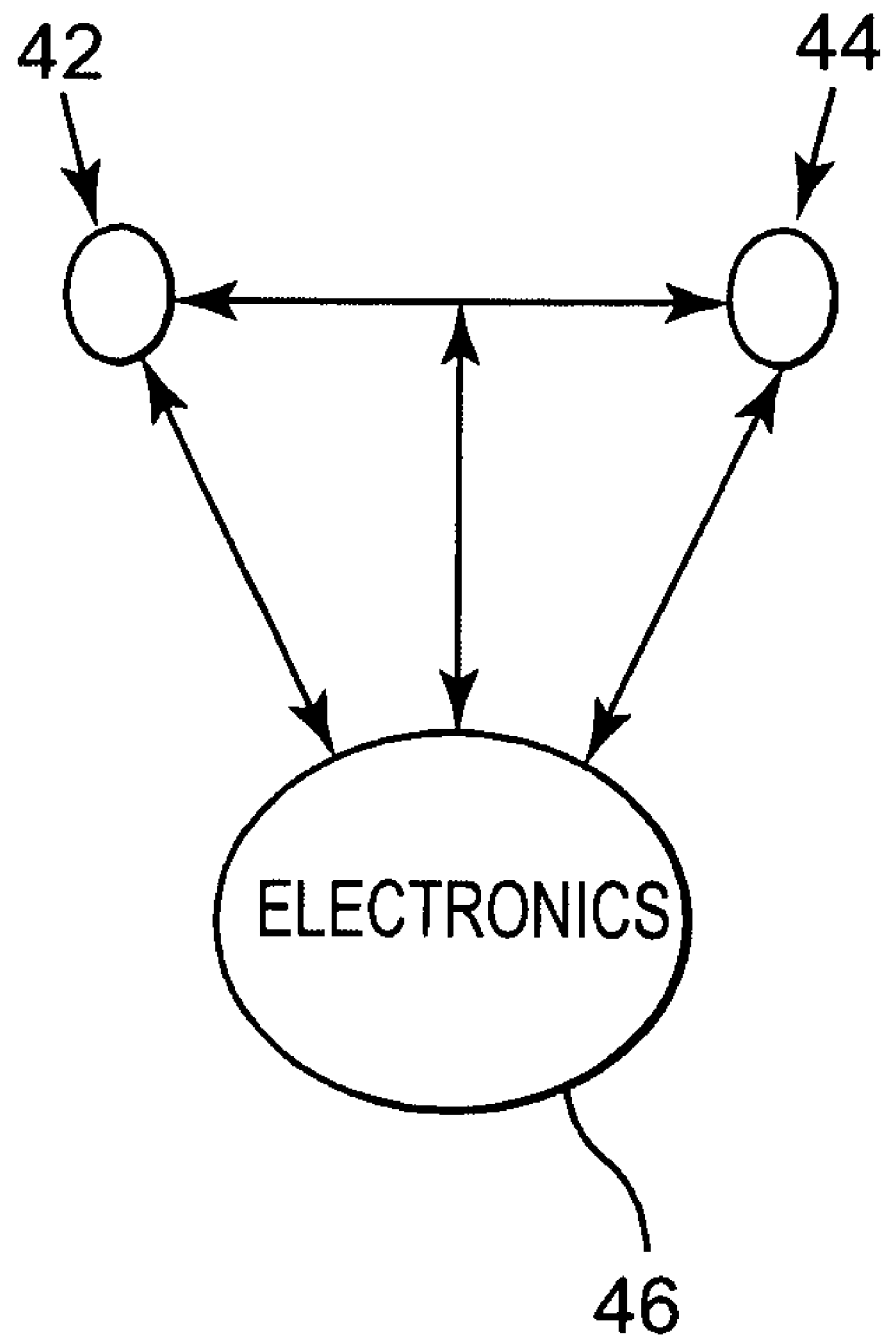
FIG. 11 is drawing illustrating coupling of sensors and/or sensors to electronics according to an embodiment of the invention.

Any means capable of comparing an intracatheter pressure to a reference pressure may be used. Overviews of how such a comparison may be made are shown in FIG. 11. For example, a first sensor 42 for detecting an intracatheter pressure may be coupled to a second sensor 44 for detecting a reference pressure. The coupled first and second sensors (42 and 44) may then be coupled to electronics 46 that may interpret a signal regarding the compared pressures from the coupled first and second sensors (42 and 44). Electronics 46 may compare the pressures. The first and second sensors (42 and 44) may communicate with the electronics 46 through electrical means or through other means, e.g., telemetry. As shown in FIG. 1, the electronics 46 may be part of electronics module 32 and contained within housing 26. When the reference pressure is detected in an area of the body away from the catheter 22 or external to the body, telemetry is the preferred means of communicating the reference pressure to the electronics 46.

If catheter 22 has a leak, it is difficult to detect because the back pressure against a normally flowing catheter is not very high. Therefore, detecting an even lower pressure indicative of a leak is extremely difficult. It may be preferred to introduce a partial restriction into catheter 22 in order to create a higher back pressure than would otherwise be encountered. The partial restriction would, of course, significantly limit the delivery of therapeutic substance to delivery site 23. Pressure sensor 34 is placed between pump 28 and restrictor 48 in order to be able to detect the increased back pressure. If catheter 22 then has or develops a leak before the location of restrictor 48, a significant pressure drop or lack of pressure rise in a transient condition can be detected and a leak can more easily be detected.

Preferably, catheter 22 of implantable medical device 16 contains restriction 48 (see FIG. 3) to create back pressure within a lumen of catheter 22. Flow restrictor 48 may be placed in catheter 22 to impede the flow of fluid therapeutic substance through catheter 22. Pressure sensor 34 is in fluid communication with a lumen of catheter 22 but upstream of flow restrictor 48, i.e., between pump 28 and restrictor 48, may sense backpressure within catheter 22 resulting from restrictor 48. Creating backpressure in catheter 22 may be desirable when, for example, a leak in catheter 22 is to be detected. When back pressure is created due to restrictor 48, a leak in catheter 22 will result in a more substantial drop in intracatheter pressure than when no restrictor is present. Thus, a leak may be more easily and accurately detected when backpressure is created in the catheter.

Restrictor 48 may be any restrictor capable of creating backpressure within catheter 22 while allowing sufficient amounts of therapeutic substance (pharmacological agent) to be delivered from catheter 22. Examples of suitable flow restrictors include a valve, a tortuous path, and a permeable membrane. A preferred restrictor 48 is shown and described in co-pending U.S. Provisional Patent Application, filed Apr. 22, 2004, entitled CATHETER SYSTEM HAVING FLOW RESTRICTION AND DIAGNOSTIC SYSTEM FOR USE WITH SAME Ser. No. 60/564,473, which is hereby incorporated by reference.

Any means for detecting pressure within a catheter or a reference pressure may be used. One suitable means for detecting pressure is a diaphragm.

Figure 5:
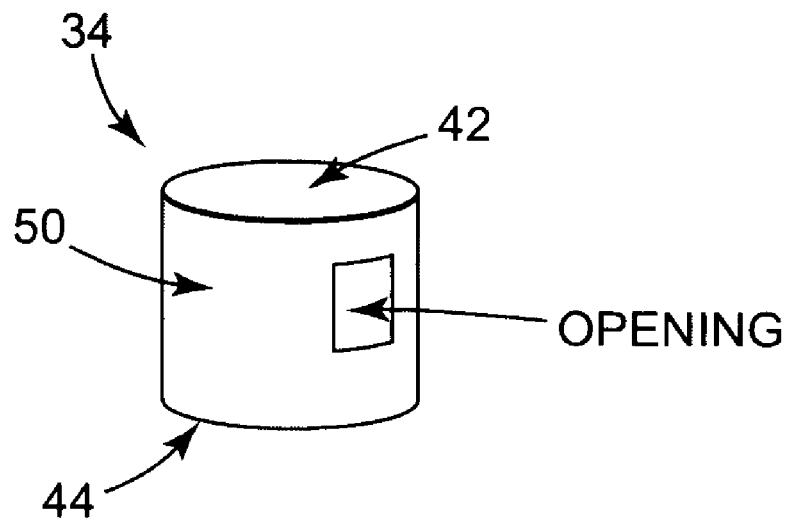
FIG. 5 is a drawing illustrating a pressure sensor of an embodiment of the invention.

FIG. 5 shows an overview of an exterior view of a pressure sensor 34, where a first sensor 42 and a second sensor 44 are housed within a sensor casing 50. The first sensor 42, which is adapted to detect a pressure within a catheter 22, is attached to the sensor casing 50 in a manner such that no or minimal fluid from the lumen of the catheter 22 may penetrate to the interior of the casing 50. The second sensor 44, which is adapted to detect a reference pressure, is also attached to the sensor casing 50 in a manner such that no or minimal fluid from may penetrate the interior of the casing 50 from the second sensor 44. The sensor casing 50 may contain an opening 52 such that wires or other objects capable of carrying a signal to electronics 46 may exit and enter the casing 50. As shown in FIG. 4, housing 26 of implantable medical device 16 may contain a vent 38 through which the second sensor 44 may detect a pressure in a body cavity of patient 18 in which implantable medical device 16 is implanted.

Figure 6:
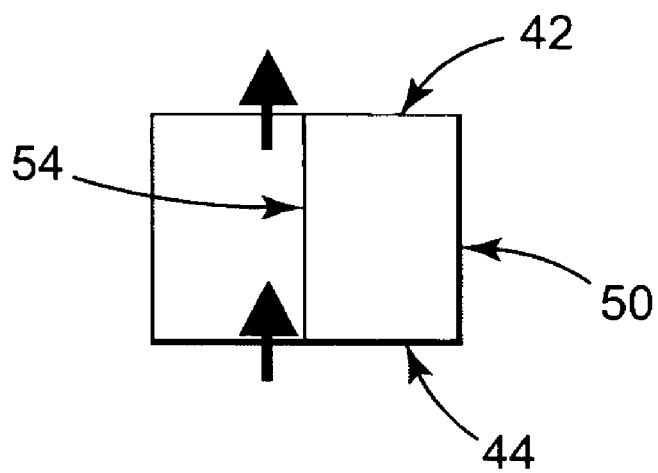
FIG. 6 is a drawing illustrating a cross section of the pressure sensor of FIG. 5.

FIG. 6 illustrates a cross section of a pressure sensor 34 of FIG. 5. First sensor 42 may be coupled through physical coupler 54 to a second sensor 44. The first and second sensors (42 and 44) may be diaphragms.

The coupler 54 and a portion of the diaphragms may move in relation to a change in pressure (reference or intracatheter). The relative movement of the coupler 54 or a diaphragm may be used to transmit information regarding a relative intracatheter pressure. The coupler 54 may be placed in contact with the first sensor 42 or second sensor 44 at any location capable of transmitting a pressure signal. When the first and second sensors (42 and 44) are diaphragms, it is preferred that the coupler 54 contact the diaphragms at or near the center of the diaphragms. It is also preferred that the area of the contact between the coupler 54 and the diaphragms is small to avoid stiffening of the diaphragm and to avoid potential gravitational influences.

Figure 7A:
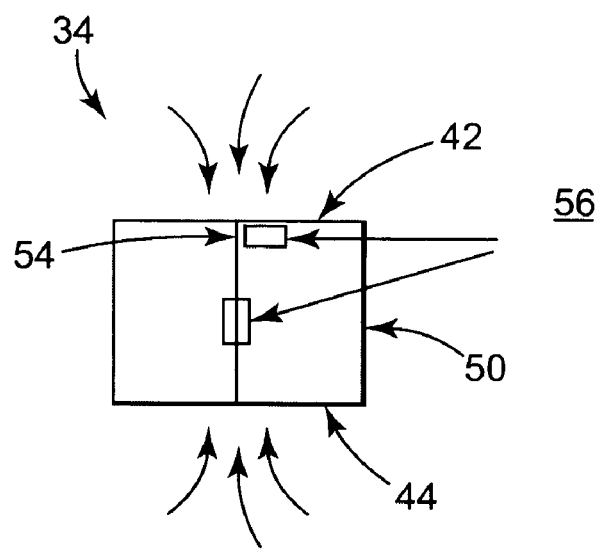
FIG. 7A is a drawing illustrating a cross section of an alternative pressure sensor of an embodiment of the invention.
Figure 7B:
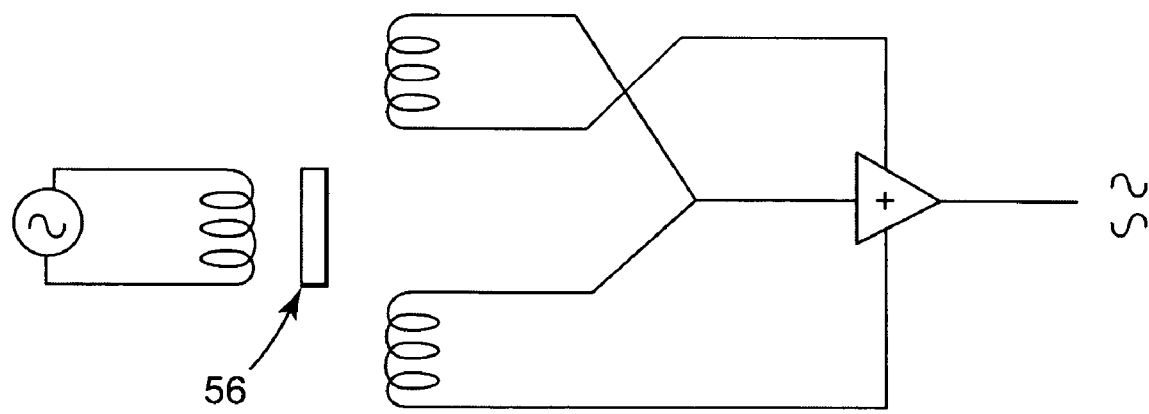
FIG. 7B is a schematic illustrating a circuit diagram of an LVDT pickoff.

FIG. 7A shows a sensor system 34 where a pick off means 56 is used to relay information to electronics 46 regarding a relative intracatheter pressure. A pick off means 56 may be placed anywhere in the sensor system 34 where the pickoff means 56 may detect a relative intracatheter pressure. For example the pick off means 56 may be placed on a sensor diaphragm or on a coupler 54. Any pick off means 56 capable of detecting a relative intracatheter pressure where first and second pressure sensors (42 and 44) are attached to a coupler 54 may be used. Suitable pick off means 56 include optical, strain, inductive (such as LVDT), capacitive, ultrasound, etc. An exemplary circuit diagram of a LVDT pick off 56 according to an embodiment of the invention is shown in FIG. 7B. Such a dual sensor 34 may simultaneously account for a reference pressure by moving in relation to a reference pressure.

Alternatively, a combination of a dual sensor incorporating a reference sensor and a mathematical adjustment of the measured pressure may be used. In this case, the referenced pressure may not be best reference pressure, or the best reference location. If a better reference pressure is available from another source, the relative pressure measured can be mathematically adjusted against the better reference.

FIG. 10A and FIG. 10B shows a modification to an implantable pump system (implantable medical device 16) that may be made to accommodate a pressure sensor 34. FIG. 10A illustrates an implantable pump system 16 without a pressure sensor 34. FIG. 10B illustrates an implantable pump system 16 with a pressure sensor system 34. With the pressure sensor system 34, the housing 26 has a bulge 58. The bulge 58 results due to an accommodation made to fit the pressure sensor 34 within the housing 26. The pressure sensor 34 may be placed in an area of the housing 26 such that it is in close proximity to electronics module 32.

Figure 8:
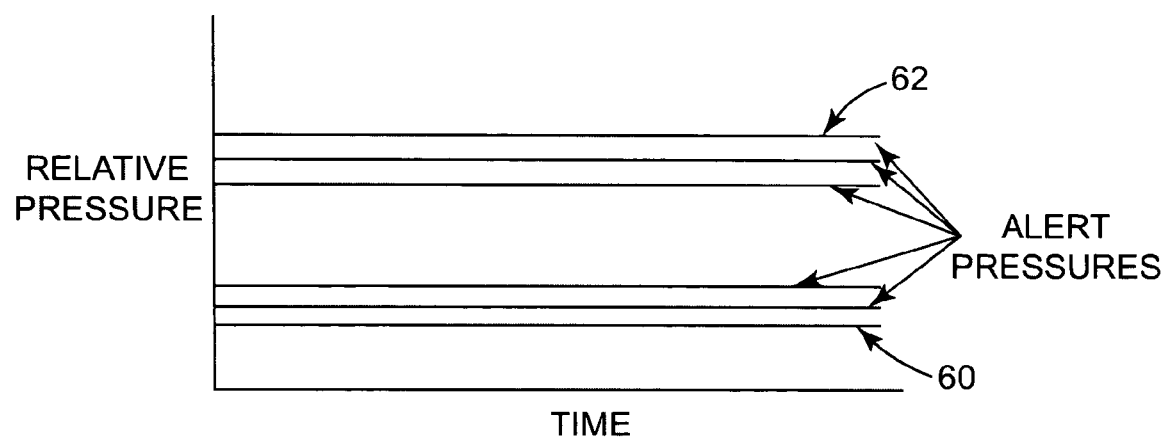
FIG. 8 is a graph of relative catheter pressure versus time illustrating alert pressures and pressure limits according to an embodiment of the invention.
Figure 9:
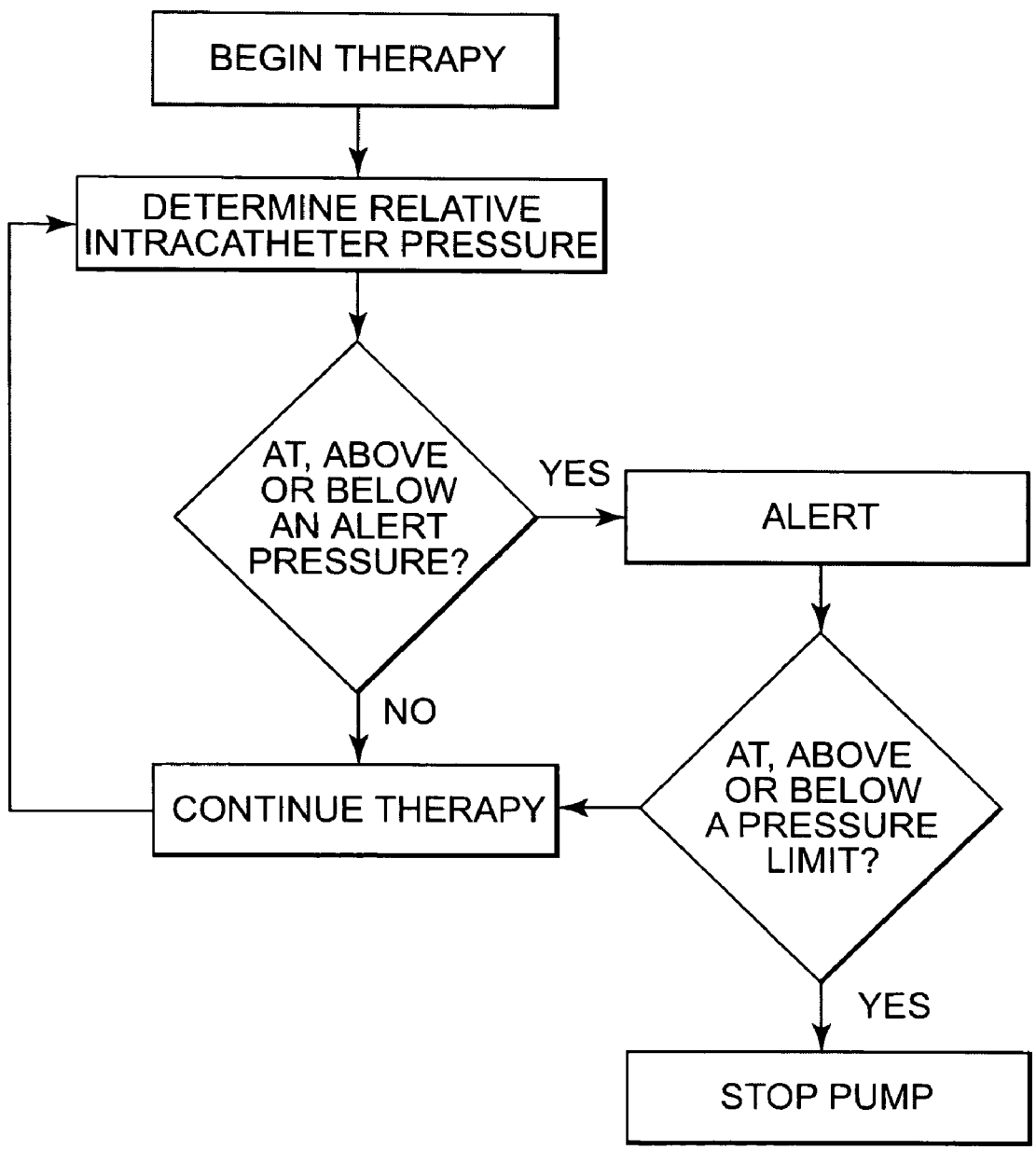
FIG. 9 is a flow chart illustrating how pressure may be used to control a pump's delivery of a therapeutic substance.

In various embodiments, the invention provides methods and systems for controlling a pump 28 and presenting an alarm if an intracatheter pressure indicative of an obstructed or leaky catheter 22 is detected. An intracatheter or relative intracatheter pressure indicative of a leak (lower limit 60 in FIG. 8) or an obstruction (upper limit 62 in FIG. 8) or pressures nearing such limits (alert pressures 64 in FIG. 8) transmitted from a sensor or sensor system 34 to electronics 46 may be used to stop the pump 28 or sound an alert 36. When a pressure limit (60 or 62) is detected, the pump 28 is stopped, or alternatively, the delivery rate of pump 28 may be reduced. It may be desirable to reduce the delivery rate, rather than stop pump 28, in various situations, for example when pump 28 is driving fluid through a bifurcated catheter and only one of the bifurcated lumens is obstructed. When an alert pressure, which may be a pressure limit (60 or 62), is detected an alert is issued. An alert may comprise a warning to a patient, calling an EMT, alarming a caregiver, etc.

Limits and alert pressures may be determined by a pump or catheter manufacture, or they may be determined by a caregiver, such as a physician, as experience dictates. Upper limits may be, for example, the maximum pressure an implantable pump may be capable of handling. Lower limits may be, for example, essentially zero intracatheter pressure.

It may be preferable to introduce a transient, or a change in the rate of delivery of therapeutic substance. Such a transient can be an increase or a decrease in the delivery rate but, typically, the preferred transient is an increase in the delivery rate. An example of a transient in the delivery rate is a commonly occurring bolus, whether programmed or initiated under patient control. Alternatively, such a transient could be an intentional introduced and specific change in delivery rate designed to more easily detect a catheter abnormality. Such a transient could be a dramatic increase in delivery rate but only for a short period of time. While typically boluses may last for many minutes or hours, such a transient may last only seconds or a few minutes. Such a transient wouldn't substantially change the overall dosage of therapeutic substance delivered to patient 18.

Implantable medical device 16 may look for a characteristic signature from pressure sensor 34 upon initiation of, during or following a transient in the delivery rate. It would be characteristic of a normal catheter for the pressure to increase upon and shortly following an increase in the delivery rate. It would also be characteristic of a normal catheter for the pressure to decrease over a decay time upon and following a decrease in delivery rate.

If the delivery rate is increased and the pressure does not correspondingly increase, the signature would be indicative of a leak in catheter 22. Contrarily, if the delivery rate is decreased and the pressure does not decay, the signature would be indicative of an obstruction in catheter 22. A higher than normal decay rate would be indicative of a slight leak in catheter 22. A slower than normal decay rate would be indicative of a slight or partial obstruction of catheter 22.

Pump 28 can be a peristaltic pump which operates with a plurality of rollers squeezing a tube containing therapeutic substance. It may be a characteristic signature of pressure readings from a catheter coupled to a peristaltic pump to have the pressure dip slightly as each of the plurality of rollers releases the tubing. This characteristic signature of pressure in catheter should occur in a normally functioning system using a peristaltic pump. If this signature is absent, it is indicative of a malfunction.

Further, the pressure occurring as each roller of a peristaltic pump releases tubing can be considered to be a transient inducing expected transient conditions in catheter 22 as discussed above.

Figure 12:
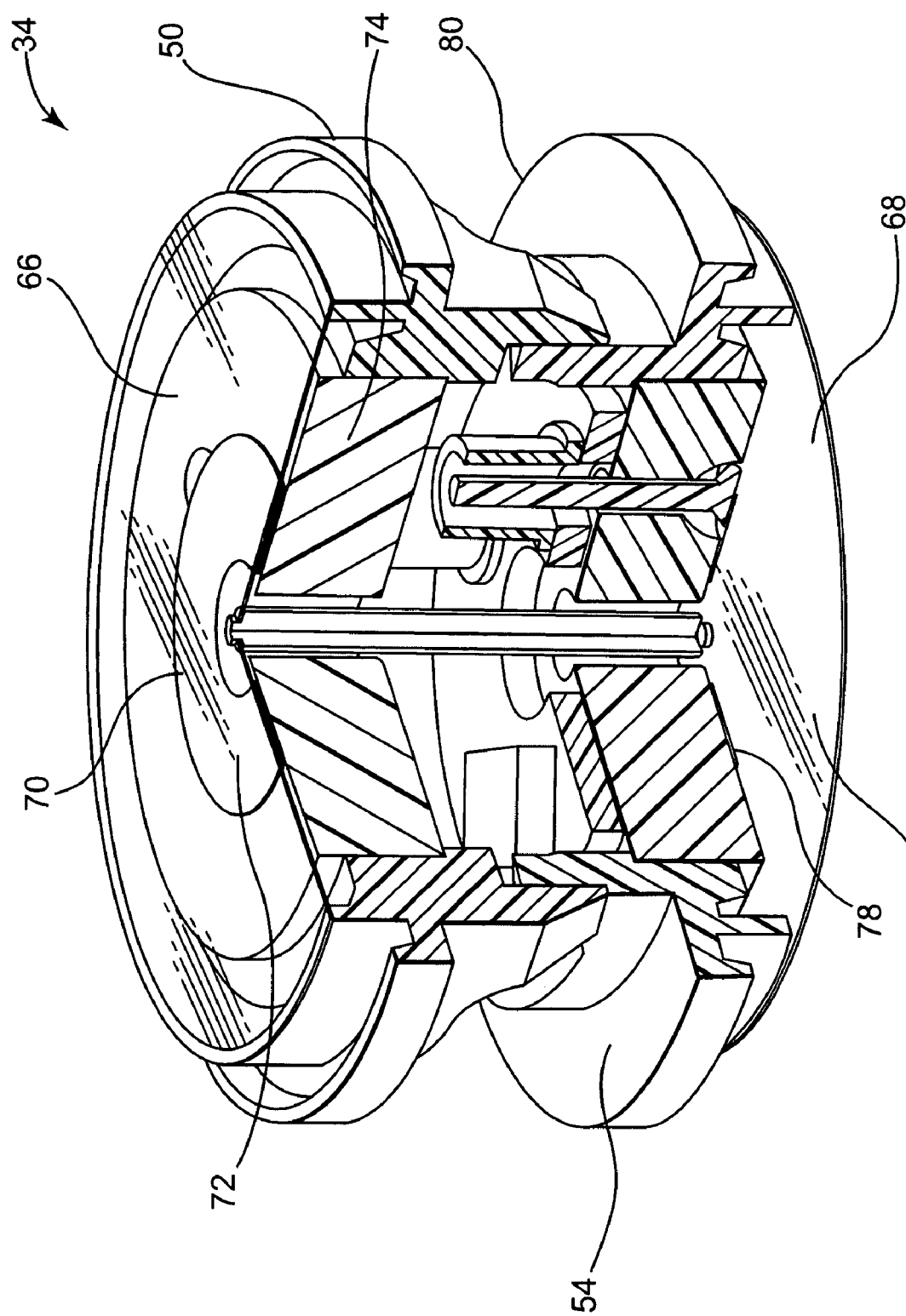
FIG. 12 illustrates a preferred embodiment of a capacitive pressure sensor.

FIG. 12 is a partial cross-sectional view of a preferred embodiment of pressure sensor 34. Pressure sensor 34 in FIG. 12 is a capacitive flow sensor utilizing two diaphragms (66 and 68). Upper diaphragm 66 is mounted to sensor casing 50. Upper diaphragm 66 is made from or is coated, at least partially, with a conductive material 70. Complementary conductive material 72 is coated on stationary sapphire insulator 74. In a preferred embodiment, a 0.002 inch gap is created between conductive materials 70 and 72. Using air as an insulator, conductive materials 70 and 72 form a capacitor. As upper diaphragm 66 moves in response to pressure changes, the capacitance created by conductive materials 70 and 72 also changes. A similar arrangement exists on the opposite end of sensor casing 50 with lower diaphragm 68. Conductive materials 76 and 78 are coated on lower diaphragm 68 and sapphire insulator 80, respectively, forming another capacitor. Coupler 54 is positioned for relative movement with, preferably against, both upper diaphragm 66 and lower diaphragm 68. Capacitive sensor 82 is sensitive to changes in both capacitances and provides the sensing output of sensor 34 illustrated in FIG. 12. Capacitive sensor 82 is conventional. A preferred implementation for capacitive sensor 82 is described in U.S. Pat. No. 5,535,752, Halperin et al, Implantable Capacitive Absolute Pressure and Temperature Monitor System, the contents of which are hereby incorporated by reference. It is worth noting that the above-described arrangement of dual diaphragms and dual capacitors actually multiplies the amount of change in capacitance with a given amount of movement in diaphragms 66 and 68. Since the pressure changes are small, the movement of diaphragms 66 and 68 are small. The capacitance change is additive resulting in twice the performance. It is preferred that coupler 54 contact diaphragms 66 and 68 in the center of the diaphragms in order to obtain the maximum movement of diaphragms 66 and 68. Coupler 54 should not significantly inhibit the movement of diaphragms 66 and 68.

Figure 13:
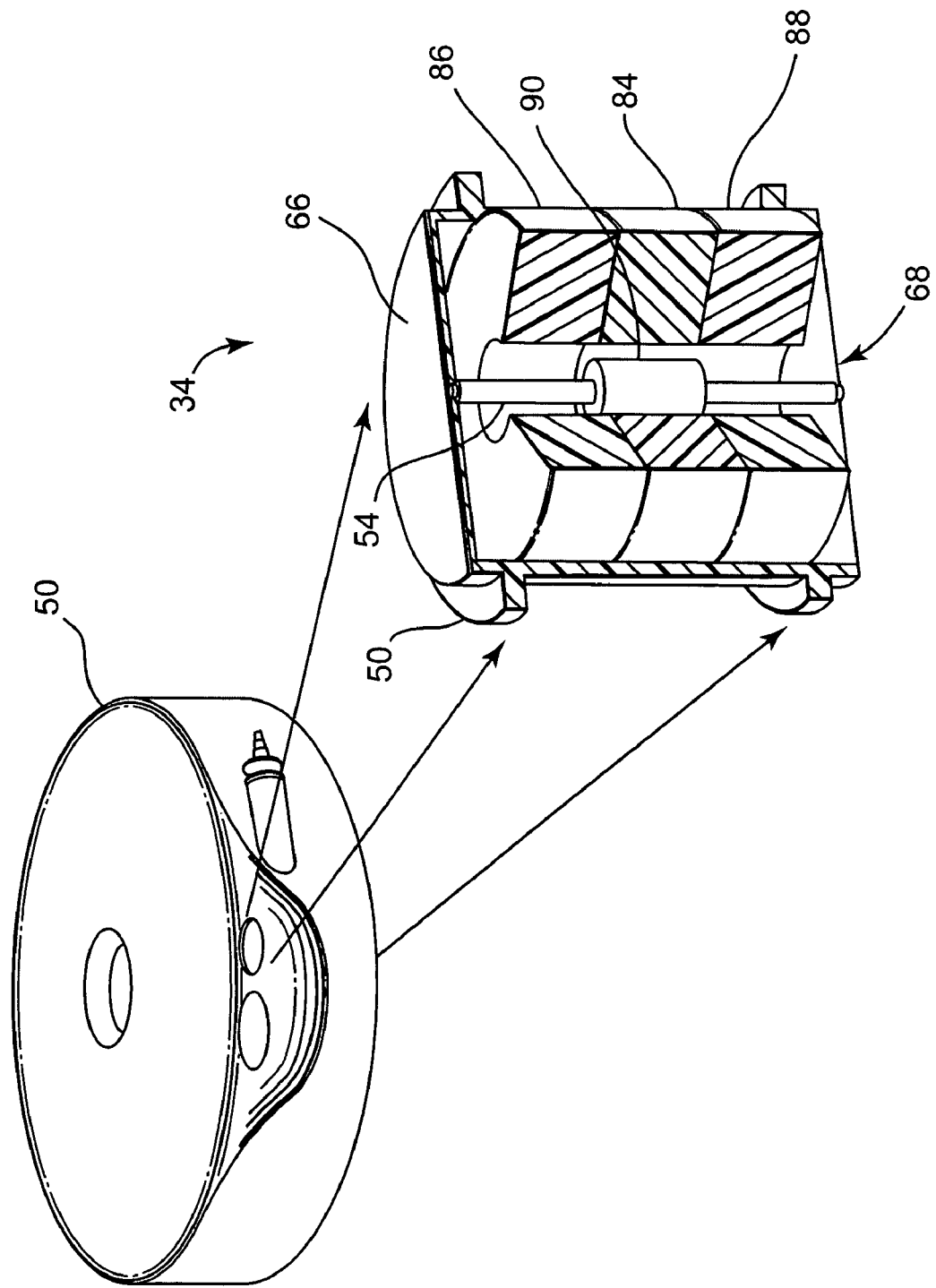
FIG. 13 illustrates a preferred embodiment of an inductive pressure sensor.

FIG. 13 illustrates an alternative embodiment of pressure sensor 34 which operates on a change in inductance. Again, sensor 34 has two diaphragms 66 and 68 with coupler 54 mounted for movement between them. A center primary coil 84 is excited with an alternative current such as a sine wave. Upper and lower secondary coils, 86 and 88 respectively, are mounted above and below primary coil 84, respectively. Magnetic element 90 is mounted for movement with coupler 54. As magnetic element 90 moves up and/or down in response to changes in pressure, the inductance induced in secondary coils 86 and 88 varies. An inductance sensor (not shown) can detect the change in these inductances and provide an output indicative of a change in pressure. Again, this arrangement doubles the effectiveness of movement in diaphragms 66 and 68 by additively combining the changes in inductance of each individual secondary coil (86 or 88).

The following discussion is intended to put some of the foregoing description in context with real world operating conditions. It is to be recognized and understood that the specific conditions, constructions and operations discussed herein may or may not be preferred and are merely indicative of a possible example of a construction, use, operating condition and the like and should not be considered to limit the scope of the invention in any way.

A pressure sensor may be placed in a drug flow path of an implantable drug delivery system, which includes a pump and a catheter. Pressure detected at a chosen location of the pressure sensor could indicate catheter complications such as blockage or leakage of the catheter. For purpose of this discussion, the sensor is assumed to be placed in a casing of a drug pump, and, preferably, a flow restriction is placed at the tip of the catheter. However, it will be recognized that the sensor may be placed anywhere in communication with the drug flow path and that the flow restriction, if desired, may be placed anywhere downstream of the sensor. Normal operation of the pump and catheter would produce a detectable backpressure over all drug delivery flow rates. A cut catheter would cause the pressure in the catheter to drop to or about zero (vs. the pressure in the fluid outside the catheter near the cut), and a blocked catheter would cause the catheter backpressure to increase significantly relative to cerebrospinal fluid (CSF) pressure, as an example of a bodily location as a delivery site. A second assumption is that the pressure drop at the catheter-tip or delivery region restriction is large enough relative to other pressure changes between the tip or region of the catheter and the sensor that other pressure changes affecting the pressure sensor reading will be insignificant in comparison, thus providing a robust measure of catheter status. Thus the purpose of this analysis is to determine, for different catheter pressure measurement approaches, what the minimum pressure change would need to be to distinguish catheter complications from background noise in the pressure signal.

The amount of pressure drop across a catheter-tip flow restriction will depend to a great extent on the pressure reference which is implemented, i.e., what is the pressure in the catheter compared against. Laboratory tests of a catheter pressure diagnostic have used a differential pressure sensor comparing catheter backpressure against atmospheric pressure. This so-called "gage" pressure reading provides a robust comparison of pressure across the flow restriction, which automatically cancels out potential reference pressure error sources such as atmospheric pressure variation (upon which physiologic pressures float). An atmospheric reference may not always be feasible in an implantable device. While ways exist to achieve an atmospheric reference with an implantable device such as plumbing a vent line across the cutaneous boundary, it may be desirable to implement another method. This discussion will look at implementations using a couple types of in-vivo pressure references, and also consider the case where there is a fixed reference, either by using a vacuum reference or a reference consisting of a sealed cavity of gas.

Physiological pressure variation: In considering catheter back pressure as a correlate for catheter flow status, typical pressure variation in the body should be taken into account. Physiologic fluid pressures typically ride on top of atmospheric pressure.

Atmospheric pressure can vary for a number of reasons.

Altitude is probably the most significant cause of physiological absolute pressure variation. Atmospheric pressure declines by approximately 1" Hg (about ½ psi) per 1000 feet increase in altitude. Putting it in perspective, one can expect about ¼ psi change in air pressure going from ground floor to the top floor of the IDS building in downtown Minneapolis (The IDS Center building is approximately 775 feet tall, with about 57 stories). Aircraft cabins are typically pressurized to 6000 feet above sea level, although unpressurized commuter and charter aircraft typically fly to 10,000 feet above sea level. Thus, the ambient pressure variation during a flight from a sea level airport could be as high as 5 psi in the case of the unpressurized aircraft with a 10,000 foot cruise altitude. Ten thousand feet is also the altitude of the highest mountain passes in the American Rocky Mountains. Travelers in mountainous regions can also experience significant variations in atmospheric pressure.

Weather is another cause of physiological pressure variation. At a given location, weather-induced atmospheric pressure variation can be on the order of 20 mm Hg (0.1 psi).

Cerebrospinal fluid (CSF) pressure, which for purpose of this discussion is the pressure reading of interest, is roughly equal to venous blood pressure, which in healthy individuals is around 0 psi at the level of the heart. However, pressure within the CSF volume can vary for a number of reasons.

Pressure may vary due to fluid column height. Pressure in the spinal column while standing, being around zero psig at the level of the heart, increases as one moves lower along the spinal column. The increase corresponds to the height of the column of salt water between the point of interest and the heart level. Typical variation is 0.04 psi/inch. The pressure difference between two points is naturally affected by the posture, with a standing posture producing maximum pressure gradient along the spinal column, and a supine posture producing minimal or zero pressure gradient.

Pressure may also vary due to disease state. Diseases such as congestive heart failure (CHF) and hydrocephalus can cause increase in CSF pressure of up to 100 mmHg (0.05 psi).

Pressure may also vary due to transient events. Straining, coughing, and other such actions on the part of the patient can cause momentary increases in physiologic pressures of up to 100 mmHg (0.05 psi). Submersion in water can cause external pressure change (and subsequent physiological fluid pressure change) on the order of 0.89 in-Hg (0.44 psi) per foot of submersion. Transient pressure events can be filtered out using algorithms commonly used to disregard outlying data, and thus will not be considered as part of the range requirements for the sensor.

These and other pressure variations may affect a pressure within a catheter. In addition, the location of a catheter within the body may affect pressure within the catheter. It will be recognized that the catheter may be placed at any location in a body where delivery of a pharmacological agent is desired and is not limited to positioning for delivery of an agent to the CSF.

Diagnostic catheter pressure change elements according to an embodiment of the invention. In an absolute pressure system, pressure in the catheter is referenced to pressure inside a sealed chamber. The pressure in the reference chamber could be any value, including a vacuum. Since there is no reference to either atmospheric pressure or the body cavity, the sensor can detect all of the pressure changes described in section 3. Range of absolute pressures detected by the sensor would include: Atmospheric pressure 10-15 psi; Weather: add 0.01 psi to top of scale, subtract 0.01 from bottom; Posture: add 0.5 psi to top end of absolute pressure range; and Disease state: add 0.05 psi to top of pressure range.

The total absolute pressure range requirement ranges from a low end of 10 psi−0.01 psi=9.99 psi to a top end of 15 psi+0.01 psi+0.5 psi+0.05 psi=15.56 psi. Pressure ranges and recommended pressure change to detect cut or leaky catheter: A catheter back pressure of at least 15.56 psi−9.99 psi=5.57 psi is preferably maintained in the catheter relative to the surrounding body fluids, to decrease the chance that the catheter diagnostic would detect a false positive due to such things as aircraft cabin pressure fluctuations, etc. Thus the absolute pressure in the catheter during normal operation may be as high as 15.56 psi+5.57 psi=21.13 psi. For the blocked catheter diagnostic, the pump would preferably deliver absolute pumping pressure higher than 21.13 psi to decrease the likelihood that catheter pressure would climb noticeably higher than normal operating pressure when blocked if high ambient fluid pressures are present.

Generally, smaller pressure changes may be used to detect a cut in a catheter if the time course of the pressure changes is taken into account in a diagnostic algorithm. Since most transient pressure events (coughing, submersion in water, etc.) tend to increase pressure, and significant decreases in pressure (altitude change) occur slowly, an abrupt decrease in pressure may indicate a cut catheter. To detect such an abrupt decrease in pressure, a pressure baseline is preferably established prior to the catheter being cut.

Barometric Reference: A separate absolute pressure sensor may be used to significantly reduce the pressure change and max absolute pressure requirements of a diagnostic pressure sensor since the largest error term, atmospheric pressure, could be eliminated from the band of pressure uncertainty. A separate absolute pressure sensor may be located, for example, either in the drug pump sensing peritoneal pressure or carried by the patient and sensing atmospheric.

An absolute pressure sensor implementation is believed to be the most straightforward and least disruptive in terms of amount of modification to the pump. A sensor similar to Medtronic, Inc.'s Chronicle™ pressure sensor could be inserted in the drug path, with electrical interface created to interface to the pump electronics. Adding a second sensor in the implant for purpose of subtracting peritoneal pressure may also be employed. With use of an external barometer a type of low-power wireless short-medium distance communications medium is preferred.

Differential Pressure Sensor: A differential pressure sensor may be used. A differential pressure sensor may be designed to measure the difference between pressures in two regions, typically by applying the pressure from one region to one side of a sensor diaphragm, and the pressure from the other region to the opposite side of the sensing diaphragm. In this way the diaphragm deflection is proportional to the difference in pressure between the two regions.

One system uses as reference a pressure in the vicinity of the pump (peritoneal pressure), and the other system uses a pressure in the CSF at the tip of the catheter.

For a reference in the peritoneum, Error terms due to atmospheric pressure variation and global physiological pressure change would be expected to cancel. Some errors due to local physiological pressure change may still exist, for instance if the patient lies atop the pump and pressure increases locally due to the weight of the patient being supported by tissue and fluid around the pump. The magnitude of this local pressure may be taken into consideration. Additional pressure error may be due to postural effects on pressure difference between the pump implant site and the tip of the catheter, which as described previously could cause up to 0.5 psi max variation in differential pressure. Thus a catheter backpressure of about 0.5 psi or greater is preferred.

A vent port to the pump to access peritoneal pressure may be included, and internal plumbing to conduct peritoneal fluid pressure from the port to the backside of the sensor diaphragm may be included in a pump system. Preferably, fluid would be in contact with both sides of the sensing diaphragm in operation of such a system. Pickoff methods or mechanical designs that allow fluid to press against both sides of a diaphragm while keeping the pickoff hardware from contacting fluids are preferred.

For a reference at the tip of the catheter or at a delivery region of the catheter, it is believed that all error terms described in this document would substantially cancel out. Any means may be used to locate a pressure sensor at a catheter tip. For example, a dual-lumen catheter or a separate catheter may be employed to conduct fluid pressure from the tip of the catheter to the sensor in the drug pump. A minimal pressure drop across catheter tip may be sufficient for detection.

A dual lumen catheter, one lumen of which terminates with a flow restriction, is preferred. A second catheter connector port may be added on the pump and internal plumbing to conduct CSF pressure from the connector port to the backside of the diaphragm may be added. Preferably, a pressure sensor design that allows fluid contact with both sides of the diaphragm is employed. Further, it may be desirable to periodically flush the reference lumen, as it is a stagnant column of CSF. One way to allow flushing would be to connect the reference lumen to a catheter access port of an implantable pump system. A second catheter access port may be used to flush the main drug delivery line. Alternatively, a means for accessing both lines from a single catheter access port (without allowing pressure communication between the two lumens during normal pump operation) was may be used.

So far this discussion has so far assumed a constant flow rate of drug delivery producing a long-term pressure trend, and technical issues in separating out changes in catheter back pressure from pressure changes caused by other influences. If the drug delivery method were changed from a constant flow to a pulsed approach, then the time-course of pressure changed could be used as an additional diagnostic. In this case, the buildup and dissipation of pressure caused by flow pulsation could be distinguishable from other pressure changes because of its characteristic signature, and because the pump controls the timing of the pressure pulsations and thus pressure changes which do not correspond with programmed drug flow pulses may be largely ignored. A system could thus be implemented using a single absolute pressure sensor largely ignoring long-term pressure changes in favor of concentrating on the pressure signature in the time window of pump pulsations.

Pulsed flow would create pressure spikes instead of a constant back pressure at a given flow rate. An advantage of a pulsed delivery is that the pressure spike amplitude may be easier to detect than a steady-state pressure, since at a given average flow rate the instantaneous flow rate during the pulse, assuming the pulses are spaced apart in time, will be much higher than if the flow rate was constant over the same time period. Also, a diagnostic algorithm may look at the pressure signal only during the pulse, decreasing the importance of a reference pressure to compare against catheter backpressure since the pressure sensor can obtain a baseline pressure reading just before the pulse. In other words, the pressure change caused by the pulse relative to the pressure just before the pulse may be used. Also, the pressure decay characteristic after the pulse pressure peak may provide additional information that a steady state pressure may not be able to provide (because the time constant of the pressure decay is defined by the capacity of the catheter and the forward resistance to flow). A cut catheter would exhibit a very rapid pressure decay (and in fact probably wouldn't show a substantial peak), since there would likely be little or no forward resistance. A blocked catheter may show a slow decay, or if completely blocked may show no decay at all, and may just find a new steady-state pressure level due to the increased volume of fluid trying to fill the blocked catheter. The point along the catheter where the blockage has occurred may be predicted by noting the pressure rise for a given volume increase. A blockage nearer the pump would decrease the capacity of the catheter to absorb additional fluid volume behind the blockage, and thus would likely show a very large pressure increase (relative to one where the blockage further away from the pump). A blockage at the end of the catheter would be expected conversely exhibit much lower pressure increase after a pulse since there is more capacity to absorb the additional volume of fluid.

Thus, embodiments of the invention are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical device for delivering a liquid therapeutic substance to a delivery site in a patient comprising:
   a reservoir holding a supply of said fluid therapeutic substance;
   a catheter having a proximal end, a delivery region and a lumen extending from said proximal end to said delivery region, said proximal end of said catheter being operatively coupled to said reservoir, said delivery region of said catheter being adapted to be placed proximate said delivery site in said patient, said therapeutic substance adapted to be delivered through said lumen to said patient;
   a sensing device operatively coupled with said lumen of said catheter being capable of detecting a pressure of said therapeutic substance in said lumen;
   a controller operatively coupled to said sensing device, said controller being capable of taking an action is response to said pressure in said lumen;
   wherein said therapeutic substance comprises a fluid;
   wherein said therapeutic substance comprises a liquid;
   wherein said sensing device is further capable of detecting a reference pressure outside of said lumen and wherein said controller is capable of taking action in response to relative pressures between said pressure in said lumen and said reference pressure outside of said lumen;
   wherein said location outside of said lumen is in proximity to said delivery region of said catheter; and
   wherein said lumen is a first lumen and wherein said catheter has a second lumen and wherein said location outside of said first lumen is in said second lumen.

2. An implantable medical device as in claim 1 wherein said sensing device comprises:
   a first pressure sensor operatively coupled with said first lumen of said catheter being capable of detecting a pressure of said therapeutic substance in said first lumen; and
   a second pressure sensor being capable of detecting a pressure at a location outside of said first lumen.

3. An implantable medical device as in claim 1 wherein said action is taken when said pressure exceeds a predetermined level.

4. An implantable medical device as in claim 3 wherein said action is based upon an obstruction in said first lumen.

5. An implantable medical device as in claim 1 wherein said first lumen of said catheter has a restriction and wherein said sensing device is positioned between said reservoir and said restriction.

6. An implantable medical device as in claim 5 wherein said action is taken when said pressure drops below a predetermined level.

7. An implantable medical device as in claim 6 wherein said action is based upon a leak of said catheter.

8. An implantable medical device as in claim 5 wherein said action is taken when said pressure has a characteristic signature.

9. An implantable medical device as in claim 8 wherein said characteristic signature follows a transient in delivery rate of said therapeutic substance.

10. An implantable medical device as in claim 9 wherein said transient comprises a rise in said delivery rate of said therapeutic substance.

11. An implantable medical device as in claim 9 wherein said transient comprises a fall in said delivery rate of said therapeutic substance.

12. An implantable medical device as in claim 9 wherein said transient comprises a rise and subsequent fall in said delivery rate of said therapeutic substance.

13. An implantable medical device as in claim 12 wherein said characteristic signature is a function of a decay time of said pressure following said fall of said delivery rate of said therapeutic substance.

14. An implantable medical device as in claim 12 wherein said characteristic signature is a function of an increase in said pressure in response to an increase of said delivery rate.

15. An implantable medical device as in claim 5 further comprising a pump fluidly coupled between said reservoir and said sensing device, said pump being capable of driving said therapeutic substance through said catheter under pressure.

16. An implantable medical device as in claim 15 wherein said pump comprises a peristaltic pump.

17. An implantable medical device as in claim 16 wherein said peristaltic pump comprises a tubular structure and a plurality of rollers driving said therapeutic substance through said tubular structure, said peristaltic pump creating a pressure dip each time one of said plurality of rollers lifts off of said tubular structure and wherein said characteristic signature comprises said pressure dropping below a predetermined threshold in combination with a lack of said pressure dip.

18. An implantable medical device as in claim 17 wherein said action comprises modifying operation of said pump.

19. An implantable medical device as in claim 1 wherein said action comprises ceasing delivery of said therapeutic substance to said patient.

20. An implantable medical device as in claim 19 further comprising a pump fluidly coupled between said reservoir and said catheter, said pump being capable of driving said therapeutic substance through said catheter under pressure.

21. An implantable medical device as in claim 20 wherein said action comprises modifying operation of said pump.

22. A drug delivery system for delivering a liquid therapeutic substance to a delivery site in a patient comprising:
   an implantable medical device, comprising:
      a reservoir holding a supply of said fluid therapeutic substance; and
      a pump fluidly coupled to said reservoir, said pump being capable of fluidly driving said therapeutic substance to said delivery site under pressure;
   a catheter having a proximal end, a delivery region and a lumen extending from said proximal end to said delivery region, said proximal end of said catheter being operatively coupled to said reservoir, said delivery region of said catheter being adapted to be placed proximate said delivery site in said patient, said therapeutic substance adapted to be delivered through said lumen to said patient;
   a sensing device operatively coupled with said lumen of said catheter being capable of detecting a pressure of said therapeutic substance in said lumen;
   a controller operatively coupled to said sensing device, said controller being capable of taking an action in response to said pressure in said lumen;
   wherein said sensing device is further capable of detecting a reference pressure outside of said lumen and wherein said controller is capable of taking action in response to relative pressures between said pressure in said lumen and said reference pressure outside of said lumen;
   wherein said location outside of said lumen is in proximity to said delivery region of said catheter; and
   wherein said lumen is a first lumen and wherein said catheter has a second lumen and wherein said location outside of said first lumen is in said second lumen.

23. A drug delivery system as in claim 22 wherein said sensing device comprises:
a first pressure sensor operatively coupled with said first lumen of said catheter being capable of detecting a pressure of said therapeutic substance in said first lumen; and
a second pressure sensor being capable of detecting a pressure at a location outside of said first lumen and inside of said second lumen.

24. A drug delivery system as in claim 22 wherein said action is taken when said pressure exceeds a predetermined level.

25. A drug delivery system as in claim 24 wherein said action is based upon an obstruction in said first lumen.

26. A drug delivery system as in claim 22 wherein said first lumen of said catheter has a restriction and wherein said sensing device is positioned between said reservoir and said restriction.

27. A drug delivery system as in claim 26 wherein said restriction is located near said distal end of the said catheter.

28. A drug delivery system as in claim 26 wherein said action is taken when said pressure drops below a predetermined level.

29. A drug delivery system as in claim 28 wherein said action is based upon a leak of said catheter.

30. A drug delivery system as in claim 29 wherein said action is taken when said pressure has a characteristic signature.

31. A drug delivery system as in claim 30 wherein said characteristic signature follows a transient in delivery rate of said therapeutic substance.

32. A drug delivery system as in claim 31 wherein said transient comprises a rise in said delivery rate of said therapeutic substance.

33. A drug delivery system as in claim 31 wherein said transient comprises a fall in said delivery rate of said therapeutic substance.

34. A drug delivery system as in claim 31 wherein said transient comprises a rise and subsequent fall in said delivery rate of said therapeutic substance.

35. A drug delivery system as in claim 34 wherein said characteristic signature is a function of a decay time of said pressure following said fall of said delivery rate of said therapeutic substance.

36. A drug delivery system as in claim 34 wherein said characteristic signature is a function of an increase in said pressure in response to an increase of said delivery rate.

37. A drug delivery system as in claim 22 wherein said pump comprises a peristaltic pump.

38. A drug delivery system as in claim 37 wherein said peristaltic pump comprises a tubular structure and a plurality of rollers driving said therapeutic substance through said tubular structure, said peristaltic pump creating a pressure dip each time one of said plurality of rollers lifts off of said tubular structure and wherein said characteristic signature comprises said pressure dropping below a predetermined threshold in combination with a lack of said pressure dip.

39. A drug delivery system as in claim 38 wherein said action comprises stopping operation of said pump.

40. A drug delivery system as in claim 22 wherein said action comprises ceasing delivery of said therapeutic substance to said patient.

41. A drug delivery system as in claim 40 wherein said action comprises stopping operation of said pump.

* * * * *